United States Patent [19]

Stoss et al.

[11] Patent Number: 4,559,351

[45] Date of Patent: Dec. 17, 1985

[54] DIHYDROPYRIDINE DERIVATIVES OF 1,4:3,6-DIANHYDROHEXITOLS

[75] Inventors: Peter Stoss, Illertissen; Matyas Leitold, Biberach, both of Fed. Rep. of Germany

[73] Assignee: Heinrich Mack Nachf., Illertissen, Fed. Rep. of Germany

[21] Appl. No.: 624,642

[22] Filed: Jun. 26, 1984

Related U.S. Application Data

[63] Continuation-in-part of Ser. No. 556,737, Nov. 30, 1983, abandoned.

[30] Foreign Application Priority Data

Dec. 29, 1982 [DE] Fed. Rep. of Germany ....... 3248548

[51] Int. Cl.[4] .................. C07D 493/00; A61K 31/455
[52] U.S. Cl. ..................................... 514/338; 546/270
[58] Field of Search ..................... 546/270; 424/266; 514/338

[56] References Cited

U.S. PATENT DOCUMENTS

| 2,143,324 | 1/1939 | Krantz | 167/65 |
| 3,799,934 | 3/1974 | Meyer et al. | 260/294.8 G |
| 4,154,839 | 5/1979 | Wehinger et al. | 424/266 |
| 4,166,855 | 9/1979 | Wehinger et al. | 424/266 |
| 4,364,953 | 12/1982 | Klessing et al. | 424/266 |

FOREIGN PATENT DOCUMENTS

| 2935451 | 3/1981 | Fed. Rep. of Germany . |
| 1027891 | 4/1966 | United Kingdom . |
| 1356374 | 6/1974 | United Kingdom . |

Primary Examiner—Henry R. Jiles
Assistant Examiner—Dale A. Bjorkman
Attorney, Agent, or Firm—Charles J. Knuth; Peter C. Richardson; Lorraine M. Donaldson

[57] ABSTRACT

The present invention relates to new acyl derivatives of 1,4:3,6-dianhydrohexitols, processes for their preparation and drugs containing the same. The new compounds have a cardiovascular effect and can be used as antihypertensive agents, as peripheral and central vasodilators and as coronary therapeutic agents.

11 Claims, No Drawings

DIHYDROPYRIDINE DERIVATIVES OF 1,4:3,6-DIANHYDROHEXITOLS

CROSS-REFERENCE TO RELATED APPLICATIONS

This application is a continuation-in-part of application Ser. No. 556,737, filed Nov. 30, 1983 now abandoned.

BACKGROUND OF THE INVENTION

The present invention relates to new acyl derivatives of 1,4:3,6-dianhydrohexitols, processes for their preparation and their usage as a drug, especially for influencing the cardiovascular system.

It is known that specified 1,4:3,6-dianhydrohexitols show interesting pharmacological properties. So a diuretic affect has been described for 1,4:3,6-dianhydro-D-glucitol (isosorbide) e.g. Proc. Soc. exp. Biol.Med. 119, 39 (1965) as well as for 1,4:3,6-dianhydro-D-mannitol (isomannide), e.g. U.S. Pat. No. 2,143,324 1,4:3,6-dianhydro-D-glucitol-2,5-dinitrate (isosorbide dinitrate as well as its metabolite, isosorbide-5-nitrate, are known coronary vasodilators that are used therapeutically.

Moreover some acyl derivatives of 1,4:3,6-dianhydrohexitols have already been examined pharmacologically, e.g. in DOS 2 221 080 containing among others lower alkanoyl derivatives and benzoyl derivatives of the isosorbide mononitrates and in DOS 3 028 289 where among others nicotinoyl-1,4:3,6-dianhydrohexitol nitrates are described. Furthermore mononicotinoyl- and dinicotinoyl-1,4:3,6-dianhydrohexitols were recognized as being effective on the vascular system in BP No. 1 027 891.

SUMMARY OF THE INVENTION

The present invention is directed to new acyl derivatives of 1,4:3,6-dianhydrohexitols of the general formula I

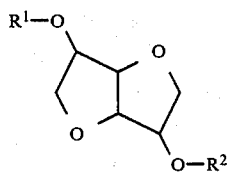

and pharmaceutically acceptable salts of compounds being capable of salt formation, wherein $R^1$ is hydrogen, a lower acyl radical with 2 to 5 carbon atoms, pyridylcarbonyl or nitro ($NO_2$), and $R^2$ is a 1,4-dihydropyridylcarbonyl radical of the general formula II

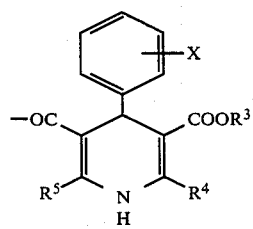

X is hydrogen, 1, 2 or 3 of the same of different substituents selected from the group consisting of alkoxy, alkyl, cyano, dialkylamino, halogen, nitro and trifluoromethyl, or methylenedioxy, $R^3$ is a straight-chain or branched, saturated or unsaturated hydrocarbon radical with 1 to 5 cabon atoms and, if necessary the chain can be interrupted by an oxygen atom and/or the hydrocarbon radical, if necessary, can be substituted by a cyano group, $R^4$ and $R^5$ are the same or different and mean in each case a lower alkyl group.

Unless something different is indicated alkyl groups means also in groupings such as alkoxy or the like such alkyl groups with 1 to 5 carbon atoms, preferably with 1 to 3 carbon atoms.

DETAILED DESCRIPTION OF THE INVENTION

The acyl derivatives of the 1,4:3,6-dianhydrohexitols discussed herein include in particular the stereoisomeric basic compounds which can be converted into each other by epimerization, which are listed in the following, namely:

1,4:3,6-dianhydro-L-iditol (isoidide) of the following structure

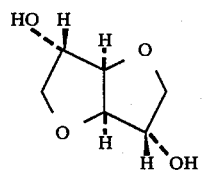

wherein the OH groups each show exo-configuration in the 2-position and in the 5-position, or 1,4:3,6-dianhydro-D-glucitol (isosorbide) of the following structure

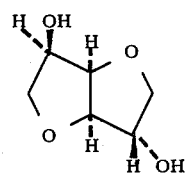

that shows a 2-exo-position and a 5-endo-position OH group and whose O-derivatives can thus occur in two isomeric forms, or 1,4:3,6-dianhydro-D-mannitol (isomannide) of the following structure

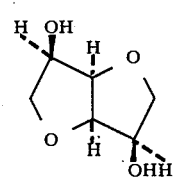

showing two endo-position OH groups.

In this respect the radicals $R^1$ and $R^2$ in the general formula I can in each case occupy both the 2-position and the 5-position.

Contrary to the glucitol derivatives, a distinction between a substitution in the 2-position and the 5-position is not possible for iditol and mannitol derivatives. J. A. Mills gives a brief summary on the stereochemistry of 1,4:3,6-dianhydrohexitols in Advances in Carbohydrate Chemistry 10, 1–53 (1955).

1,4:3,6-dianhydrohexitols represent optically active molecules. The acyl radicals of the general formula II have a chiral centre at the C-4 of the 1,4-dihydropyridine ring. Therefore the compounds of the general formula I according to the present invention occur as diastereoisomers, one pair of diastereoisomers each existing for each radical $R^1$ and also for each radical $R^2$. Both the diastereoisomer mixtures and the separated uniformly configurated components are the subject of this invention.

According to the prior art chiral 1,4-dihydropyridine carboxylic esters are already known, e.g. DOS No. 2 117 571, DOS No. 2 549 568, DOS No. 2 650 013 and DOS No. 2 935 451. Among these are also those ones that were separated into optically active antipodes. However, no derivatives of 1,4:3,6-dianhydrohexitols are present in any of the cases already described.

The intramolecular combination of the 1,4-dihydropyridylcarbonyl radical, which is known as pharmacophorically active group with the also pharmacologically active class of 1,4:,3,6-dianhydrohexitols, which was made here for the first time is novel. It allows a further differentiation of effect, makes possible new insights into structure-activity interrelations, opens additional fields of application and thus represents an enrichment of the therapeutical possibilities.

Especially preferred compounds of the general formula I are such in which $R^1$ is hydrogen.

A group of compounds according to the present invention comprises such in which the 1,4:3,6-dianhydrohexitol is isosorbide, the oxygen atom being substituted in the 2-position (or in the 5-position) with $R^1$ and the oxygen atom being substituted with $R^2$ in the 5-position (or in the 2-position), $R^3$, $R^4$ and $R^5$ meaning moreover preferably methyl and $R^1$ meaning acetyl and X hydrogen or $R^1$ meaning nitro and X 3-nitro or $R^1$ meaning nitro and X 4-cyano, or $R^1$ meaning hydrogen and X hydrogen or $R^1$ meaning hydrogen and X nitro or $R^1$ meaning butanoyl and X 2-nitro or $R^1$ meaning nitro and X hydrogen or $R^1$ meaning acetyl and X 3-nitro or $R^1$ meaning acetyl and X 2-nitro or $R^1$ meaning hydrogen and X 2-nitro or $R^1$ meaning nitro and X 4-fluoro or $R^1$ meaning nitro and X 3-trifluoromethyl or $R^1$ meaning nitro and X 3,4-methylenedioxy or $R^1$ meaning nitro and X 2-nitro.

Another class of compounds according to the present invention comprises such in which the 1,4:3,6-dianhydrohexitol is isosorbide, the oxygen atom being substituted with $R^2$ in the 2-position (or in the 5-position) and the oxygen atom being substituted with $R^1$ in the 5-position (or in the 2-position), and comprises preferably such compounds in which $R^3$, $R^4$ and $R^5$ each are methyl and $R^1$ is furthermore nitro and X hydrogen or $R^1$ is nitro and X 3-nitro or $R^1$ is hydrogen and X 3-nitro or $R^1$ is hydrogen and X 2-nitro or $R^1$ is acetyl and X 2-nitro or $R^1$ is acetyl and X 3-nitro or $R^1$ is nitro and X 2,4-methylenedioxy or $R^1$ is nitro and X 4-fluoro or $R^1$ is nitro and X 2-methoxy or $R^1$ is nitro and X 4-cyano or $R^1$ is nitro and X 3-trifluoromethyl.

Compounds in which $R^1$ is nitro, X is 3-nitro, $R^3$ is butyl and $R^4$ and $R^5$ each are methyl; or $R^1$ is nitro, X is 3-nitro, $R^3$ is isopropyl and $R^4$ and $R^5$ each are methyl; or $R^1$ is nitro. X is 3-nitro, $R^3$ is ethyl and $R^4$ and $R^5$ each are methyl; or $R^1$ is nitro, X is 3-nitro, $R^3$ is allyl and $R^4$ and $R^5$ each are methyl; or $R^1$ is nitro, X is 3-nitro, $R^3$ is isobutyl and $R^4$ and $R^5$ each are methyl; or $R^1$ is nitro, X is 3-nitro, $R^3$ is tert.-butyl and $R^4$ and $R^5$ each are methyl; or $R^1$ is nitro, X is 3-nitro, $R^3$ is 3-ethoxy propyl and $R^4$ and $R^5$ each are methyl are also preferred.

The present invention also comprises pharmaceutical preparations which contain at least one compound according to the present invention and a pharmaceutically acceptable carrier or a pharmaceutically acceptable diluent. The present invention relates furthermore to the use of the compounds according to the present invention for controlling cardiovascular diseases and therapies for controlling cardiovascular diseases in mammals including men, the living being being treated with an effective amount of a compound according to the present invention.

It was found that the compounds according to the present invention are obtained if (A) an arylidene-$\beta$-ketocarboxylic ester of the general formula III

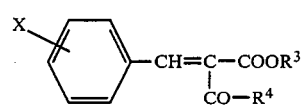

wherein X, $R^3$ and $R^4$ have the indicated meaning is reacted according to generally known procedures with an enaminocarboxylic acid-(1,4:3,6-dianhydrohexitol) ester of the general formula IV

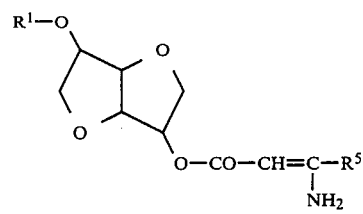

wherein $R^1$ and $R^5$ have the indicated meaning or (B) an aldehyde of the general formula V

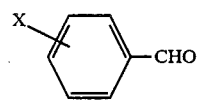

in which X has the indicated meaning is reacted according to generally known procedures with a $\beta$-ketocarboxylic ester of the general formula VI

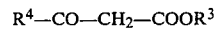

$$R^4—CO—CH_2—COOR^3 \qquad VI$$

wherein $R^3$ and $R^4$ have the indicated meaning and with an enaminocarboxylic acid-(1,4:3,6-dianhydrohexitol) ester of the general formula IV, in which $R^1$ and $R^5$ have the indicated meaning or (C) an aldehyde of the general formula V, in which X has the indicated meaning, is reacted according to generally known procedures with an enaminocarboxylic ester of the general formula VII

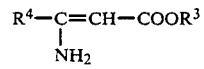

wherein R³ and R⁴ have the indicated meaning and with a β-ketocarboxylic acid-(1,4:3,6-dianhydrohexitol) ester of the general formula VIII

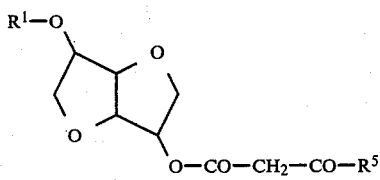

wherein R¹ and R⁵ have the indicated meaning or (D) an arylidene-β-ketocarboxylic ester of the general formula III, in which X, R³ and R⁴ have the indicated meaning, is reacted according to generally known procedures with a β-ketocarboxylic acid-(1,4:3,6-dianhydrohexitol) ester of the general formula VIII, in which R¹ and R⁵ have the indicated meaning and with ammonia, and if an acyl derivative of the general formula I obtained in this fashion is converted, if necessary, to a salt according to generally known procedures.

When carrying out the processes (A) to (D) the substances participating in the reaction are each used in approx. molar amounts. The ammonia used is expediently added in excess. The reaction can be effected without solvent, but also in water or in all organic solvents being inert under the reaction conditions. These include preferably alcohols such as methanol, ethanol, propanol and isopropanol or ethers such as diethyl ether, dioxane, tetrahydrofuran, glycol monomethyl ether and glycol dimethyl ether or glacial acetic acid, pyridine, acetonitrile, dimethyl formamide or dimethyl sulfoxide.

The reaction temperatures are variable in wide ranges and range from 2° to 200° C. in general. It is preferable to work at 50° to 120° C., especially at the boiling temperature of the respective solvent.

The reactions can be carried out at normal pressure, but also at increased pressure; usually it is worked at normal pressure.

The isolation and purification of the compounds according to the present invention is carried out in customary fashion. In some cases the reaction products crystallize directly after the completed reaction. In other cases it is expedient to distil off the solvent under vacuum, subsequently to allow the residue to crystallize and then to recrystallize from an adequate solvent, if necessary.

The reactions (A) to (D) are known per se. They represent variants of the Hantz pyridine synthesis as they were partly described by Knoevenagel, Ber.Dtsch.Chem. Ges. 31, 738 (1898). More recent summaries are found e.g. in Arzneim.-Forsch. 31, 407 (1981), Angew. Chem. 93, 755 (1981) and in Drugs of the Future VI, 427 (1981).

The starting products of the general formulae IV and VIII used according to the invention are new. The other ones are already known or can be prepared according to methods known in the literature. The new compounds IV and VIII can be prepared according to generally known procedures. Thus the β-ketocarboxylic acid-(1,4:3,6-dianhydrohexitol) esters of the general formula VIII can be obtained, for example, from the corresponding 1,4-3,6-dianhydrohexitol derivatives of the general formula IX

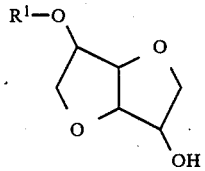

wherein R¹ has the indicated meaning, by reaction with diketene or by means of transesterification with β-ketocarboxylic acid lower alkyl esters (compare e.g. Houben-Weyl, Methoden der Organischen Chemie, vol. VII/4, 230 et sequ. (1968).

Examples for the esters of the general formula VIII are:
Acetoacetic-(5-isosorbide) ester
Acetoacetic-(2-isosorbide) ester
Acetoacetic isomannide ester,
Acetoacetic isoidide ester,
Acetoacetic-(5-isosorbide-2-nitrate) ester,
Acetoacetic-(2-isosorbide-5-nitrate) ester,
Acetoacetic-(5-isomannide-2-nitrate) ester,
Acetoacetic-(5-isoidide-2-nitrate) ester,
Acetoacetic-(5-isosorbide-2-acetate) ester,
Acetoacetic-(2-isosorbide-5-acetate) ester,
Acetoacetic-(5-isomannide-2-acetate) ester,
Acetoacetic-(5-isoidide-2-acetate) ester,
Acetoacetic-(5-isosorbide-2-butyrate) ester,
Acetoacetic-(2-isosorbide-5-butyrate) ester,
Acetoacetic-(5-isosorbide-2-nicotinate) ester,
Acetoacetic-(2-isosorbide-5-nicotinate) ester,
Propionyl acetic-(5-isosorbide-2-nitrate) ester,
Propionyl acetic-(2-isosorbide-5-nitrate) ester,
Propionyl acetic-(5-isosorbide) ester,
Propionyl acetic-(2-isosorbide) ester,
Propionyl acetic-(5-isosorbide-2-acetate) ester,
Propionyl acetic-(2-isosorbide-5-acetate) ester,
Propionyl acetic isomannide ester,
Propionyl acetic isoidide ester.

Also the enaminocarboxylic acid-(1,4:3,6-dianhydrohexitol) esters of the general formula IV can be prepared according to generally known procedures from the β-ketocarboxylic acid-(1,4:3,6-dianhydrohexitol) esters of the general formula VIII by reaction with ammonia.

The following are mentioned as examples for the esters of the general formula IV:
β-aminocrotonic acid-(5-isosorbide) ester,
β-aminocrotonic acid-(2-isosorbide) ester,
β-aminocrotonic acid isomannide ester,
β-aminocrotonic acid isoidide ester,
β-aminocrotonic acid-(5-isosorbide-2-nitrate) ester,
β-aminocrotonic acid-(2-isosorbide-5-nitrate) ester,
β-aminocrotonic acid-(5-isomannide-2-nitrate) ester,
β-aminocrotonic acid-(5-isoidide-2-nitrate) ester,
β-aminocrotonic acid-(5-isosorbide-2-acetate) ester,
β-aminocrotonic acid-(2-isosorbide-5-acetate) ester,
β-aminocrotonic acid-(5-isomannide-2-acetate) ester,
β-aminocrotonic acid-(5-isoidide-2-acetate) ester,
β-aminocrotonic acid-(5-isosorbide-2-butyrate) ester,
β-aminocrotonic acid-(2-isosorbide-5-butyrate) ester,
β-aminocrotonic acid-(5-isosorbide-2-nicotinate) ester,
β-aminocrotonic acid-(2-isosorbide-5-nicotinate) ester,
β-amino-β-ethyl acrylic acid-(5-isosorbide-2-nitrate) ester,
β-amino-β-ethyl acrylic acid-(2-isosorbide-5-nitrate) ester, β-amino-β-ethyl acrylic acid-(5-isosorbide) ester,
β-amino-β-ethyl acrylic acid-(2-isosorbide) ester,
β-amino-β-ethyl acrylic acid-(5-isosorbide-2-acetate) ester,
β-amino-β-ethyl acrylic acid-(2-isosorbide-5-acetate) ester,
β-amino-β-ethyl acrylic acid isomannide ester,
β-amino-β-ethyl acrylic acid isoidide ester.

The compounds of the general formula I according to the present invention, in which $R^2$ has the indicated meaning and $R^1$ is hydrogen, can furthermore be prepared according to the variant by transesterification of the compounds of the general formula I, wherein $R^1$ is a lower acyl radical with 2 to 5 carbon atoms or a pyridyl carbonyl radical and $R^2$ has the indicated meaning according to generally known procedures with a lower alcohol such as methanol, ethanol, etc. or by subjecting said compounds to a hydrolysis in the presence of acids or bases.

Hydrolysis is preferably carried out in the presence of an organic solvent miscible with water at temperatures ranging from 0° to 150° C. Alcohols such as methanol, ethanol, propanol, isopropanol and then dioxane, tetrahydrofuran, glacial acetic acid, dimethyl formamide, dimethyl sulfoxide and others come into consideration as solvents. Both acids such as sulfuric acid, hydrochloric acids and the like and bases such as alkali hydroxides, alkali alcoholates, etc. come into consideration as hydrolysis agents.

The transesterification with lower alcohols can be carried out in the presence of alkali alcoholates such as sodium or potassium methylate or ethylate or in the presence of basic ion exchangers such as Dowex. Here the alcohol used for transesterification is preferably also used as solvent.

Vice versa, compounds of the general formula I, in which $R^1$ is a lower acyl radical with 2 to 5 carbon atoms or a pyridyl carbonyl radical and $R^2$ has the indicated meaning can be prepared by acylating compounds of the general formula I, in which $R^1$ is hydrogen and $R^2$ has the indicated meaning according to generally known procedures by means of a corresponding acid chloride or acid anhydride (variant F).

Due to the two possible opposite configurations at the C-4 atoms of the 1,4-dihydropyridine ring and the chirality of the 1,4:3,6-dianhydrohexitols two diastereoisomers are formed during each of the preparation variants A to D. These differ in their chemical and physical properties and can thus be separated from each other by means of known methods. The following are mentioned e.g. as separating processes: recrystallization from appropriate, inert solvents, separation by means of thin-layer chromatography or column chromatography or separation by means of high-pressure liquid chromatography.

When using the pair of diastereoisomers in the preparation variants E and F the corresponding pair of diastereoisomers is again obtained in each case as reaction product. If one proceeds from the separated, uniformly configurated components, uniform components of the same configuration as the starting product are obtained according to E and F.

Both the diastereoisomer mixtures and the separated, uniformly configurated components can be used as pharmaceutical active substances and form part of the present invention.

The acyl derivatives of the 1,4:3,6-dianhydrohexitols according of the general formula I according to the present invention and their salts possess valuable pharmacological properties. Due to their cardiovascular effect they can be used e.g. as antihypertensive agents, as peripheral and central vasodilators and as coronary therapeutic agents.

The new active substances can be converted to customary pharmaceutical formulation with known methods using appropriate carrier substances and additives or solvents. The formulation can be administered in customary fashion, preferably orally or parenterally, i.e. intramuscularly, subcutaneously, intravenously or intraperitoneally. The carrier or the diluent are chosen in accordance with the desired mode of administration. In the case of an oral administration the drugs according to the present invention can e.g. be used in the form of tablets, capsules, lozenges, powders, syrups, elexirs, aqueous solutions and suspensions or the like in accordance with standard pharmacological practice. The ratio between the active substance and the carrier will naturally depend on the chemical nature, the solubility and the stability of the active substance and on the desired dosage. The pharmaceutical compositions contain the active substance according to the invention preferably in an amount of about 20 to 95%. In the case of tablets for oral administration carriers which are commonly used include lactose, sodium citrate and salts of phosphoric acid. Additives such as starch, lubricants such as magnesium stearate, sodium lauryl sulfate and talc are customarily used in tablets. For oral administration in capsule form, appropriate diluents are lactose and high-molecular polyethylene glycols. If aqueous solutions or suspensions are required for oral administration, the active substance may be combined with emulsifiers and suspending agents. If desired, certain sweetening and/or flavouring agents can be added. For parenteral administration, sterile solutions of the active substance are usually prepared and the pH value of the solutions is suitably adjusted and buffered. For intravenous administration the total concentration of the solutes is to be controlled in order to adjust the preparation isotonically.

Although the physician administering the drug will ultimately determine the dosage to be used, it can be proceeded from the fact that the individual dosage of the substances according to the present invention will generally range from 0.10 to 3.0 mg/kg body weight, preferably from 0.15 to 1.0 mg/kg body weight in anti-angina pectoris and anti-hypertensive agents. For application in humans for the treatment of angina pectoris attacks 2 to 4 sublingual tablets or solutions as oral spray can be used per day. For the treatment of hypertension and for the prophylactic treatment of angina pectoris 2 to 4 capsules, coated pills, tablets or 1 to 2 suppositories should be administered per day. It may be quite sufficient in some cases to administer less than the above-mentioned dosage, whereas the upper limits can also be exceeded in other cases.

The invention is illustrated by the following examples. The indicated melting points are not corrected. $[\alpha]_D^{20}$ means the optical rotation at 20° C., sodium-D-line. The kind of solvent and the concentration of the solution measured in gl 100 ml are given in brackets. As far as values are indicated for more than one compound in the examples, isomers being isolated separately are concerned.

EXAMPLE 1

5-(1,4-dihydro-2,6-dimethyl-3-methoxycarbonyl-4-phenyl-5-pyridylcarbonyl)-isosorbide-2-acetate (a) Isosorbide-2-acetate-5-acetoacetate: 155 ml diketene are added dropwise to 376 g isosorbide-2-acetate and 2 ml triethyl amine at 80° C. under stirring and the mixture is kept at this temperature for one hour. The formed reaction product is recovered in oily form and is used in the next step without further purification.

(b) Isosorbide-2-acetate-5-(3-amino) crotonate: the crude product from (a) is dissolved in 1 l ethanol. A strong ammonia flow is introduced until saturation and the mixture is allowed to stand at room temperature for 2 hours following this. Then short boiling is effected and a cooling in an ice bath. During this the reaction product crystallizes, which is isolated by means of sucking off. After recrystallization from ethanol 350 g with the melting point 123°–124° C. are obtained.

(c) 40.8 g benzylidene acetoacetic methyl ester and 54.2 g isosorbide-2-acetate-5-(3-amino) crotonate are heated in 200 ml ethanol with reflux for 8 hours. The deposit (42 g) obtained after cooling is sucked off and recrystallized from ethanol. In this fashion the one isomer, (+)-5-(1,4-dihydro-2,6-dimethyl-3-methoxycarbonyl-4-phenyl-5-pyridylcarbonyl)-isosorbide-2-acetate, melting point 189°–190° C., $[\alpha]_D^{20}+45.37$ (c=1.047, ethanol) is obtained.

The other isomer, (−)-5-(1,4-dihydro-2,6-dimethyl-3-methoxycarbonyl-4-phenyl-5-pyridylcarbonyl)-isosorbide-2-acetate, is recovered from the mother liquors by means of concentration and recrystallization from ethanol. Melting point 183°–184° C., $[\alpha]_D^{20}-52.87$ (c=1.012, ethanol).

EXAMPLE 2

2-[1,4-dihydro-2,6-dimethyl-3-(2-methoxy-ethoxycarbonyl)-4-(3-nitrophenyl)-5-pyridylcarbonyl]-isosorbide-5-nitrate (a) isosorbide-5-nitrate-2-acetoacetate: 155 ml diketene are added dropwise to 362 g isosorbide-5-nitrate and 2 ml triethyl amine at 80° C. under stirring and the mixture is kept at this temperature for one hour. The formed reaction product is recovered in oily form and is used in the next step without further purification.

(b) Isosorbide-5-nitrate-2-(3-amino) crotonate: The crude product obtained from (a) is reacted with ammonia in accordance with example 1(b). 375 g reaction product are obtained, which melts at 96.5°–98.5° C. after recrystallization from ethanol.

(c) 15.1 g 3-nitro-benzaldehyde, 16.0 g acetoacetic-(2-methoxyethyl) ester and 27.4 g isosorbide-5-nitrate-2-(3-amino) crotonate are heated in 300 ml ethanol under reflux for 16 hours. The deposit obtained after cooling is sucked off and recrystallized from ethanol. 17.6 g (+)-2-[1,4-dihydro-2,6-dimethyl-3-(2-methoxy-ethoxycarbonyl)-4-(3-nitrophenyl)-5-pyridylcarbonyl]-isosorbide-5-nitrate are obtained, melting point 201° C., $[\alpha]_D^{20}+113.2$ (c=0.349, acetone). 11.5 g of the other isomer, (+)-2-[1,4-dihydro-2,6-dimethyl-3-(2-methoxy-ethoxycarbonyl)-4-(3-nitrophenyl)-5-pyridylcarbonyl]-isosorbide-5-nitrate, are recovered from the mother liquors by means of concentration and recrystallization from isopropanol. Melting point 124° C., $[\alpha]_D^{20}+26.1$ (c=0.556, acetone).

EXAMPLE 3

5-[1,4-dihydro-2,6-dimethyl-3-methoxycarbonyl-4-(3-nitrophenyl) 5-pyridylcarbonyl]-isosorbide-2-nitrate (a) Isosorbide-2-nitrate-5-acetoacetate: the preparation is carried out in analogous fashion to example 1 (a) from isosorbide-2-nitrate and diketene. The substance is used as oily crude product for the further reaction.

(b) A solution of 27.5 g isosorbide-2-nitrate-5-acetoacetate, 15.1 g 3-nitrobenzaldehyde and 11.5 g 3-aminocrotonic methyl ester in 100 ml ethanol is heated under reflux for 20 hours. Then it is concentrated under vacuum and the residue is is mixed with ether. After being allowed to stand from some time, 21 g of the more difficultly soluble isomer crystallize, which is purified by means of recrystallization from methanol (+)-5-[1,4-dihydro-2,6-dimethyl-3-methoxycarbonyl-4-(3-nitrophenyl)-5-pyridylcarbonyl] isosorbide-2-nitrate is obtained, melting point 182.5° C. (decomposition), $[\alpha]_D^{20}+33.9$ (c=0.087, ethanol).

The etherial mother liquor is concentrated and the residue is purified by means of recrystallization from toluene. The other isomer, (−)-5-[1,4-dihydro-2,6-dimethyl-3-methoxycarbonyl-4-(3-nitrophenyl)-5-pyridylcarbonyl]-isosorbide-2-nitrate is obtained, melting point 160° C., $[\alpha]_D^{20}-51.4$ (c=0.292, ethanol).

EXAMPLE 4

5-[1,4-dihydro-2,6-dimethyl-3-methoxycarbonyl-4-(4-cyanophenyl)-5-pyridylcarbonyl]-isosorbide-2-nitrate 3 g ammonia are introduced into a solution of 27.5 g isosorbide-2-nitrate-5-acetoacetate (example 3 a) in 100 ml ethanol. Then this mixture is mixed with 22.9 g (4-cyanobenzylidene)acetoacetic methyl ester and heated under reflux for 20 hours a weak ammonia flow being passed through the solution at the beginning. Concentration is effected and the residue is absorbed in toluene/ether at a ratio of 1:1, in the course of which crystallization sets in. The one isomer is obtained by means of recrystallization from ethanol, melting point 172° C. (decomposition), $[\alpha]_D^{20}+72.1$ (c=0.985, acetone).

EXAMPLE 5

5-(1,4-dihydro-2,6-dimethyl-3-methoxycarbonyl-4-phenyl-5-pyridylcarbonyl) isosorbide 20 g (+)-5-(1,4-dihydro-2,6-dimethyl-3-methoxycarbonyl-4-phenyl-5-pyridylcarbonyl)-isosorbide-2-acetate with a melting point of 189°–190° C. (example 1) are suspended in 100 ml methanol and mixed with 1 ml 35% methanolic sodium methylate solution. A clear solution is formed under stirring at room temperature from which a deposit is precipitated after some time. This deposit is sucked off and recrystallized from ethanol. 14 g (+)-5-(1,4-dihydro-2,6-dimethyl-3-methoxycarbonyl-4-phenyl-5-pyridylcarbonyl) isosorbide are obtained, melting point 193° C., $[\alpha]_D^{20}+44.2$ (c=1.209, ethanol).

When using the laevorotatory isomer, (−)-5-(1,4-dihydro-2,6-dimethyl-3-methoxycarbonyl-4-phenyl-5-pyridylcarbonyl) isosorbide with a melting point of 183°–184° C. (example 1) the corresponding isomer, (−)-5-(1,4-dihydro-2,6-dimethyl-3-methoxycarbonyl-4-phenyl-5-pyridylcarbonyl isosorbide is obtained in analogous fashion, which crystallizes with 0.25 mol water. Melting point 120°–121° C., $[\alpha]_D^{20}-67.5$ (c=1.015, ethanol).

EXAMPLE 6

5-[1,4-dihydro-2,6-dimethyl-3-methoxycarbonyl-4-(3-nitrophenyl)-5-pyridylcarbonyl] isosorbide 5.0 g (−)-5-[1,4-dihydro-2,6-dimethyl-3-methoxycarbonyl-4-(3-nitrophenyl)-5-pyridylcarbonyl]-isosorbide-2-acetate (example 12) and 0.5 g sodium hydroxide are dissolved in 20 ml methanol and stirred for some time at room temperature. The formed deposit is sucked off and recrystallized. 3.9 g (−)-5-[1,4-dihydro-2,6-dimethyl-3-methoxycarbonyl-4-(3-nitrophenyl)-5-pyridylcarbonyl] isosorbide are obtained. The substance crystallizes with 1 mol methanol and has a melting point of 163° C. in this form, $[\alpha]_D^{20} -37.6$ (c=1.077, ethanol).

In the same fashion the corresponding isomer is obtained from (+)-5-[1,4-dihydro-2,6-dimethyl-3-methoxycarbonyl-4-(3-nitrophenyl)-5-pyridylcarbonyl] isosorbide-2-acetate (example 12), melting point 155° C., $[\alpha]_D^{20} +53.64$ (c=0,811, ethanol).

EXAMPLE 7

5-[1,4-dihydro-2,6-dimethyl-3-methoxycarbonyl-4-(2-nitrophenyl)-5-pyridylcarbonyl]-isosorbide-2-butyrate 10 g (+)-5-[1,4-dihydro-2,6-dimethyl-3-methoxycarbonyl-4-(2-nitrophenyl)-5-pyridylcarbonyl] isosorbide (example 24) are stirred with 10 g butyric anhydride and 0.1 g 4-dimethylaminopyridine at 60° C. for 30 minutes. When diluting the reaction mixture with 100 ml ether a crystalline precipitate is obtained which is sucked off and recrystallized from ethanol. Yield: 9.8 g, melting point 161°–163° C., $[\alpha]_D^{20} +182.06$ (c=1.125, acetone).

When using the laevorotatory isomer (example 24) the corresponding isomer is obtained. Melting point 153°–156° C. (from toluene/ether), $[\alpha]_D^{20} -195.53$ (c=1.097, acetone).

The following compounds are obtained according to one of the methods indicated in examples 1 to 7.

EXAMPLE 8

5-[1,4-dihydro-2,6-dimethyl-3-methoxycarbonyl-4-(2-nitrophenyl)-5-pyridylcarbonyl]-isosorbide-2-nitrate (a) Isosorbide-2-nitrate-5-(3-amino) crotonate is obtained from isosorbide-2-nitrate-5-acetoacetate (example 3), melting point 118° C. (from ethanol).

(b) Melting point 217°–219° C. (decomposition) (from acetonitrile), $[\alpha]_D^{20} +195.8$ (c=0.036, ethanol).

Melting point 79°–81° C. (from acetonitrile), $[\alpha]_D^{20} -268.0$ (c=0.25, ethanol).

EXAMPLE 9

2-[1,4-dihydro-2,6-dimethyl-3-methoxycarbonyl-4-(2-nitrophenyl)-5-pyridylcarbonyl]-isosorbide-5-nitrate Melting point 207° C. (decomposition) (from acetonitrile), $[\alpha]_D^{20} -168.2$ (c=0.217, ethanol).

Melting point 186°–187° C. (from ethanol), $[\alpha]_D^{20} +162.6$ (c=0.376, ethanol).

EXAMPLE 10

5-(1,4-dihydro-2,6-dimethyl-3-methoxycarbonyl-4-phenyl-5-pyridylcarbonyl)-isosorbide-2-nitrate Melting point 188°–189° C. (decomposition) (from ethanol), $[\alpha]_D^{20} +11.7$ (c=0.256, ethanol).

EXAMPLE 11

2-(1,4-dihydro-2,6-dimethyl-3-methoxycarbonyl-4-phenyl-5-pyridylcarbonyl)-isosorbide-5-nitrate Melting point 147°–148° C. (from toluene), $[\alpha]_D^{20} +115.1$ (c=0.364, ethanol).

Melting point 146° C. (from toluene), $[\alpha]_D^{20} +66.96$ (c=1.064, ethanol).

EXAMPLE 12

5-[1,4-dihydro-2,6-dimethyl-3-methoxycarbonyl-4-(3-nitrophenyl)-5-pyridylcarbonyl]-isosorbide-2-acetate Melting point 216°–217° C. (from ethanol), $[\alpha]_D^{20} +48.39$ (c=0.248, ethanol).

Melting point 94°–97° C. (from ether), $[\alpha]_D^{20} -16.6$ (c=0.965, ethanol).

EXAMPLE 13

5-[1,4-dihydro-2,6-dimethyl-3-methoxycarbonyl-4-(2-nitrophenyl)-5-pyridylcarbonyl]-isosorbide-2-acetate Melting point 212° C. (from acetonitrile), $[\alpha]_D^{20} +48.74$ (c=0.658, acetone).

Melting point 205°–207° C. (from ethanol), $[\alpha]_D^{20} -157.8$ (c=0.952, acetone).

EXAMPLE 14

2-[1,4-dihydro-2,6-dimethyl-3-methoxycarbonyl-4-(3-nitrophenyl)-5-pyridylcarbonyl]-isosorbide-5-nitrate Isomer mixture: melting point 204° C. (decomposition) (from ethanol), $[\alpha]_D^{20} +74.0$ (c=1.051, acetone).

EXAMPLE 15

2-[1,4-dihydro-2,6-dimethyl-3-methoxycarbonyl-4-(3-nitrophenyl)-5-pyridylcarbonyl]isosorbide (a) Isosorbide-2-(3-amino) crotonate: melting point 140° C. (from ethanol).

(b) Melting point 215° C. (from ethanol), $[\alpha]_D^{20} +83.25$ (c=1.003, acetone).

EXAMPLE 16

2-[1,4-dihydro-2,6-dimethyl-3-butoxycarbonyl-4-(3-nitrophenyl)-5-pyridylcarbonyl]-isosorbide-5-nitrate Melting point 193°–194° C. (from ethanol), $[\alpha]_D^{20} +104.8$ (c=0.501, acetone).

Melting point 170°–171° C. (from methanol), $[\alpha]_D^{20} +34.6$ (c=0.224, acetone).

EXAMPLE 17

2-[1,4-dihydro-2,6-dimethyl-3-isopropoxycarbonyl-4-(3-nitrophenyl)-5-pyridylcarbonyl]-isosorbide-5-nitrate Isomer mixture: melting point 183°–184° C. (decomposition) from isopropanol), $[\alpha]_D^{20} +119.5$ (c=0.544, acetone).

EXAMPLE 18

2-[1,4-dihydro-2,6-dimethyl-3-ethoxycarbonyl-4-(3-nitrophenyl)-5-pyridylcarbonyl]-isosorbide-5-nitrate Isomer mixture: melting point 161° C. (from ethanol), $[\alpha]_D^{20} +60.5$ (c=0.991, acetone).

EXAMPLE 19

2-[1,4-dihydro-2,6-dimethyl-3-allyloxycarbonyl-4-(3-nitrophenyl)-5-pyridylcarbonyl]-isosorbide-5-nitrate Isomer mixture: melting point 144° C. (from ethanol), $[\alpha]_D^{20} +70.8$ (c=1.024, acetone).

EXAMPLE 20

2-[1,4-dihydro-2,6-dimethyl-3-isobutoxycarbonyl-4-(3-nitrophenyl)-5-pyridylcarbonyl]-isosorbide-5-nitrate Isomer mixture: melting point 173° C. (decomposition) (from ethanol), $[\alpha]_D^{20} +62.0$ (c=1.016, acetone).

EXAMPLE 21

2-[1,4-dihydro-2,6-dimethyl-3-(tert.-butoxycarbonyl)-4-(3-nitrophenyl)-5-pyridylcarbonyl]-isosorbide-5-nitrate Melting point 192° C. (decomposition) (from methanol) $[\alpha]_D^{20} +24.6$ (c=1.035, acetone).

Crystallized with 0.25 mol water: melting point 122°-123° C. (from isopropanol), $[\alpha]_D^{20} +110.2$ (c=0.935, acetone).

EXAMPLE 22

2-[1,4-dihydro-2,6-dimethyl-3-methoxycarbonyl-4-(2-nitrophenyl)-5-pyridylcarbonyl]isosorbide Melting point 192°-194° C. (from ethanol), $[\alpha]_D^{20} +290.0$ (c=1.006, acetone).

Crystallized with 0.25 mol water: melting point 172°-177° C. (from ethanol), $[\alpha]_D^{20} -228.6$ (c=1.111, ethanol).

EXAMPLE 23

2-[1,4-dihydro-2,6-dimethyl-3-methoxycarbonyl-4-(2-nitrophenyl)-5-pyridylcarbonyl]-isosorbide-5-acetate (a) Isosorbide-5-acetate-2-(3-amino) crotonate: The preparation is effected from isosorbide-5-acetate via the oily isosorbide-5-acetate-2-acetoacetate as described in example 1. The substance represents a viscous oil which is used in this form for the further reaction.

(b) Melting point 198°-200° C. (from ethanol), $[\alpha]_D^{20} +304.2$ (c=1.005, acetone).

Melting point 146°-149° C. (from ethanol), $[\alpha]_D^{20} -168.7$ (c=0.990, ethanol).

EXAMPLE 24

5-[1,4-dihydro-2,6-dimethyl-3-methoxycarbonyl-4-(2-nitrophenyl)-5-pyridylcarbonyl]isosorbide (a) Isosorbide-5-(3-amino) crotonate: melting point 138° C. (from ethanol).

(b) melting point 235° C. (from acetonitrile), $[\alpha]_D^{20} +209.9$ (c=1.017, acetone).

melting point 180° C. (from ethanol), $[\alpha]_D^{20} -184.0$ (c=0.954, ethanol).

EXAMPLE 25

2-[1,4-dihydro-2,6-dimethyl-3-methoxycarbonyl-4-(3-nitrophenyl)-5-pyridylcarbonyl]-isosorbide-5-acetate Melting point 131°-134° C. (from toluene/ether), $[\alpha]_D^{20} +108.5$ (c=0.968, ethanol).

EXAMPLE 26

2-[1,4-dihydro-2,6-dimethyl-3-methoxycarbonyl-4-(3,4-methylenedioxyphenyl)-5-pyridylcarbonyl]-isosorbide-5-nitrate Melting point 189° C. (from toluene), $[\alpha]_D^{20} +124.6$ (c=1.011, acetone).

Melting point 154°-156° C. (from ethanol/ether), $[\alpha]_D^{20} +41.8$ (c=0.98, ethanol).

EXAMPLE 27

5-[1,4-dihydro-2,6-dimethyl-3-methoxycarbonyl-4-(4-fluorophenyl)-5-pyridylcarbonyl]-isosorbide-2-nitrate Melting point 167° C. (from ethanol), $[\alpha]_D^{20} +30.7$ (c=0.936, ethanol).

EXAMPLE 28

2-[1,4-dihydro-2,6-dimethyl-3-methoxycarbonyl-4-(4-fluorophenyl)-5-pyridylcarbonyl]-isosorbide-5-nitrate Crystallized with 1 mol ethanol: melting point 108°-110° C. (from ethanol), $[\alpha]_D^{20} +114.6$ (c=1.065, acetone).

EXAMPLE 29

2-[1,4-dihydro-2,6-dimethyl-3-methoxycarbonyl-4-(2-methoxyphenyl)-5-pyridylcarbonyl]-isosorbide-5-nitrate Melting point 169° C. (from ethanol), $[\alpha]_D^{20} +136.7$ (c=1.035, acetone).

EXAMPLE 30

2-[1,4-dihydro-2,6-dimethyl-3-methoxycarbonyl-4-(4-cyanophenyl)-5-pyridylcarbonyl]isosorbide-5-nitrate Melting point 140° C. (decomposition) (from methanol), $[\alpha]_D^{20} +134.4$ (c=1.019, acetone).

Melting point 110° C. (from methanol), $[\alpha]_D^{20} +22.1$ (c=0.997, acetone).

EXAMPLE 31

2-[1,4-dihydro-2,6-dimethyl-3-methoxycarbonyl-4-(3-trifluoromethylphenyl)-5-pyridylcarbonyl]-isosorbide-5-nitrate Isomer mixture: melting point 171°-172° C. (from methanol), $[\alpha]_D^{20} +73.9$ (c=1.055, acetone).

EXAMPLE 32

5-[1,4-dihydro-2,6-dimethyl-3-methoxycarbonyl-4-(3-trifluoromethylphenyl)-5-pyridylcarbonyl]-isosorbide-2-nitrate Melting point 178°-179° C. (from methanol), $[\alpha]_D^{20} +56.0$ (c=1.00, acetone).

EXAMPLE 33

2-[1,4-dihydro-2,6-dimethyl-3-(3-ethoxypropoxycarbonyl)-4-(3-nitrophenyl)-5-pyridylcarbonyl]-isosorbide-5-nitrate Crystallized with 0.5 mol water: melting point 127° C. (from ethanol), $[\alpha]_D^{20} +37.7$ (c=1.100, acetone).

EXAMPLE 34

5-[1,4-dihydro-2,6-dimethyl-3-methoxycarbonyl-4-(3,4-methylenedioxyphenyl)-5-pyridylcarbonyl]-isosorbide-2-nitrate Melting point 169°-171° C. (from ethanol), $[\alpha]_D^{20} +55.7$ (c=1.014, acetone).

EXAMPLE 35

2-[1,4-dihydro-3-ethoxycarbonyl-2-ethyl-6-methyl-4-(3-nitrophenyl)-5-pyridylcarbonyl]-isosorbide-5-nitrate Melting point 147° C. (from ethanol), $[\alpha]_D^{20} +24.42$ (c=0.819, acetone).

EXAMPLE 36

5-[1,4-dihydro-2,6-dimethyl-3-methoxycarbonyl-4-(3-nitrophenyl)-5-pyridylcarbonyl]-isomannide-2-acetate (a) Isomannide-2-acetate-5-acetoacetate: The preparation is effected in analogous fashion to example 1(a) from isomannide 2-acetate and diketene.

The substance is used as oily crude product for the further reaction.

(b) Isomannide-2-acetate-5-(3-amino) crotonate: The crude product obtained from (a) is reacted with ammonia in analogous fashion to example 1(b). Melting point 120° C. (from ethanol).

(c) Isomer mixture: melting point 184°-185° C. (from methanol) $[\alpha]_D^{20}+118$ (c=1.018, acetone).

EXAMPLE 37

5-[1,4-dihydro-2,6-dimethyl-3-methoxycarbonyl-4-(3-nitrophenyl)-5-pyridylcarbonyl]isomannide Isomer mixture: melting point 141° C. (from isopropanol), $[\alpha]_D^{20}+90.4$ (c=1.001, acetone).

EXAMPLE 38

5-[1,4-dihydro-2,6-dimethyl-3-methoxycarbonyl-4-(3-nitrophenyl)-5-pyridylcarbonyl]-isomannide-2-nitrate (a) Isomannide-5-acetoacetate-2-nitrate: The preparation is effected in analogous fashion to example 1(a) from isomannide-2-nitrate and diketene. The substance is used as oily crude product for the further reaction.

(b) Isomannide-5-(3-amino) crotonate-2-nitrate: The crude product obtained from (a) is reacted with ammonia in analogous fashion to example 1(b). Melting point 95°-96° C. (from isopropanol).

(c) Melting point 176° C. (from ethanol), $[\alpha]_D^{20}+95.4$ (c=1.074, acetone).

Melting point 153° C. (from methanol), $[\alpha]_D^{20}+176.2$ (c=1.106, acetone).

EXAMPLE 39

5-[1,4-dihydro-2,6-dimethyl-3-methoxycarbonyl-4-(3-nitrophenyl)-5-pyridylcarbonyl]-isoidide-2-acetate (a) Isoidide-2-acetate-5-acetoacetate: The preparation is effected in analogous fashion to example 1(a) from isoidide-2-acetate and diketene. The substance is used as oily crude product for the further reaction.

(b) Isoidide-2-acetate-5-(3-amino) crotonate: The crude product obtained from (a) is reacted with ammonia in analogous fashion to example 1(b). Melting point 115°-116° C. (from ethanol).

(c) Isomer mixture: melting point 150° C. (sinter as of 80° C.) (from ethyl acetate/petroleum ether), $[\alpha]_D^{20}+154.4$ (c=1.017, acetone).

EXAMPLE 40

5-[1,4-dihydro-2,6-dimethyl-3-methoxycarbonyl-4-(3-nitrophenyl)-5-pyridylcarbonyl]isoidide Isomer mixture: melting point 150° C. (sinter as of 80° C.) (from ethyl acetate/petroleum ether), $[\alpha]_D^{20}+46.4$ (c=0.991, acetone)

EXAMPLE 41

5-[1,4-dihydro-2,6-dimethyl-3-methoxycarbonyl-4-(3-nitrophenyl)-5-pyridylcarbonyl]-isosorbide-2-butyrate Melting point 109°-111° C. (from ether), $[\alpha]_D^{20}+54.26$ (c=1.069, acetone).

EXAMPLE 42

5-[1,4-dihydro-2,6-dimethyl-3-methoxycarbonyl-4-(3-nitrophenyl)-5-pyridylcarbonyl]-isosorbide-2-nicotinate Crystallized with 0.5 mol water: melting point 224°-225° C. (from dichloromethane/ether), $[\alpha]_D^{20}+21.77$ (c=0.643, acetone)

Melting point 215° C. (from methanol), $[\alpha]_D^{20}-22.9$ (c=1.109, acetone).

EXAMPLE 43

5-[1,4-dihydro-2,6-dimethyl-3-methoxycarbonyl-4-(2-chlorophenyl)-5-pyridylcarbonyl]-isosorbide-2-nitrate Melting point 193° C. (from methanol), $[\alpha]_D^{20}+130.0$ (c=0.796, acetone).

EXAMPLE 44

5-[1,4-dihydro-2,6-dimethyl-3-methoxycarbonyl-4-(2-methylphenyl)-5-pyridylcarbonyl]-isosorbide-2-nitrate Melting point 194°-195° C. (decomposition) (from methanol), $[\alpha]_D^{20}+146.0$ (c=1.011, acetone).

EXAMPLE 45

2-[1,4-dihydro-2,6-dimethyl-3-methoxycarbonyl-4-(2-methylphenyl)-5-pyridylcarbonyl]-isosorbide-5-nitrate Melting point 193° C. (decomposition) (from methanol), $[\alpha]_D^{20}+242.7$ (c=1.026, acetone).

EXAMPLE 46

2-[1,4-dihydro-2,6-dimethyl-3-methoxycarbonyl-4-(3-bromophenyl)-5-pyridylcarbonyl]-isosorbide-5-nitrate Isomer mixture: melting point 170° C. (from methanol), $[\alpha]_D^{20}+232.8$ (c=0.638, acetone).

EXAMPLE 47

5-[1,4-dihydro-2,6-dimethyl-3-methoxycarbonyl)-4-(3-bromophenyl)-5-pyridylcarbonyl]-isosorbide-2-nitrate Melting point 190° C. (from ethanol), $[\alpha]_D^{20}+147.1$ (c=0.904, acetone).

EXAMPLE 48

2-[1,4-dihydro-2,6-dimethyl-3-(2-cyanoethoxy)-carbonyl-4-(3-nitrophenyl)-5-pyridylcarbonyl]-isosorbide-5-nitrate Melting point 208° C. (decomposition) (from acetonitrile), $[\alpha]_D^{20}+155.4$ (c=1.094, acetone).

EXAMPLE 49

5-[1,4-dihydro-2,6-dimethyl-3-methoxycarbonyl-4-(3-nitrophenyl)-5-pyridylcarbonyl]-isoidide-2-nitrate (a) Isoidide-5-acetoacetate-2-nitrate: The preparation is effected in analogous fashion to example 1(a) from isoidide-2-nitrate and diketene. The substance is used as oily crude product for the further reaction.

(b) Isoidide-5-(3-amino)-crotonate-2-nitrate: The crude product obtained from (a) is reacted with ammonia in analogous fashion to example 1(b) and the oily reaction product is purified by means of a column filled with silica gel.

Melting point 149° C. (from diethyl ether), $[\alpha]_D^{20}+8.93$ (c=0.504, acetone).

Melting point 141°-142° C. (from diethyl ether), $[\alpha]_D^{20}+115.66$ (c=0.582, acetone).

EXAMPLE 50

5-[1,4-dihydro-2,6-dimethyl-3-methoxycarbonyl-4-(4-dimethylaminophenyl)-5-pyridylcarbonyl]-isosorbide-2-nitrate Melting point 138° C. (from methanol), $[\alpha]_D^{20} +60.2$ (c=0.947, acetone).

EXAMPLE 51

2-[1,4-dihydro-2,6-dimethyl-3-methoxycarbonyl-4-(2-chlorophenyl)-5-pyridylcarbonyl]-isosorbide-5-nitrate Isomer mixture: melting point 154°–157° C. (from methanol/water), $[\alpha]_D^{20} +159.7$ (c=1.021, acetone).

EXAMPLE 52

5-[1,4-dihydro-2,6-dimethyl-3-methoxycarbonyl-4-(2,4-dichlorophenyl)-5-pyridylcarbonyl]-isosorbide-2-nitrate Melting point 199°–202° C. (decomposition) (from methanol), $[\alpha]_D^{20} +131.9$ (c=0.959, acetone).

EXAMPLE 53

2-[1,4-dihydro-2,6-dimethyl-3-methoxycarbonyl-4-(3,4,5-trimethoxyphenyl)-5-pyridylcarbonyl]-isosorbide-5-nitrate Melting point 187°–188° C. (from methanol), $[\alpha]_D^{20} +127.14$ (c=0.488, acetone).

EXAMPLE 54

2-[1,4-dihydro-2,6-dimethyl-3-methoxycarbonyl-4-(4-chloro-3-nitrophenyl)-5-pyridylcarbonyl]-isosorbide-2-nitrate Melting point 150° C. (from ethanol), $[\alpha]_D^{20} +41.3$ (c=0.878, acetone).

EXAMPLE 55

2-[1,4-dihydro-2,6-dimethyl-3-methoxycarbonyl-4-(4-chloro-3-nitrophenyl)-5-pyridylcarbonyl]-isosorbide-5-nitrate Melting point 182° C. (from methanol), $[\alpha]_D^{20} +100.18$ (c=0.544, acetone).

Melting point 154° C. (from methanol), $[\alpha]_D^{20} +12.25$ (c=0.408, acetone).

EXAMPLE 56

5-[1,4-dihydro-2,6-dimethyl-3-(2-methoxyethoxycarbonyl)-4-(3-nitrophenyl)-5-pyridylcarbonyl]-isosorbide Melting point 213° C. (from ethanol), $[\alpha]_D^{20} -32.1$ (c=0.862, acetone).

EXAMPLE 57

5-[1,4-dihydro-2,6-dimethyl-3-(isopropoxycarbonyl)-4-(3-nitrophenyl)-5-pyridylcarbonyl]isosorbide Melting point 152°–153° C. (from isopropanol/diisopropyl ether). $[\alpha]_D^{20} +59.2$ (c=0.972, acetone).

EXAMPLE 58

5-[1,4-dihydro-2,6-dimethyl-3-ethoxycarbonyl-4-(3-nitrophenyl)-5-pyridylcarbonyl]isosorbide Melting point 164° C. (from ethanol), $[\alpha]_D^{20} +55.72$ (c=1.041, acetone).

EXAMPLE 59

5-[1,4-dihydro-2,6-dimethyl-3-(2-cyanoethoxy)-carbonyl-4-(3-nitrophenyl)-5-pyridylcarbonyl]-isosorbide-2-acetate Melting point 194° C. (from ethyl acetate), $[\alpha]_D^{20} -8.15$ (c=0.982, acetone).

Melting point 184° C. (from ethanol), $[\alpha]_D^{20} +31.75$ (c=0.992, acetone).

EXAMPLE 60

5-[1,4-dihydro-2,6-dimethyl-3-(2-cyanoethoxy)-carbonyl-4-(3-nitrophenyl)-5-pyridylcarbonyl]isosorbide Melting point 241° C. (from acetonitrile), $[\alpha]_D^{20} -11.96$ (c=1.003, acetone).

Melting point 181° C. (from ethyl acetate), $[\alpha]_D^{20} +6.97$ (c=1.076, acetone).

EXAMPLE 61

5-[1,4-dihydro-2,6-dimethyl-3-methoxycarbonyl-4-(2,3-dichlorophenyl)-5-pyridylcarbonyl]-isosorbide-2-acetate Melting point 219°–222° C. (from toluene) $[\alpha]_D^{25} +29.3$ (c=1.03, acetone).

Melting point 187°–190° C. (from toluene) $[\alpha]_D^{25} -65.3$ (c=1.17, acetone).

EXAMPLE 62

5-[1,4-dihydro-2,6-dimethyl-3-methoxycarbonyl-4-(2,3-dichlorophenyl)-5-pyridylcarbonyl]-isosorbide Melting point 183°–185° C. (from ethyl acetate) $[\alpha]_D^{25} +29.3$ (c=1.04, acetone).

Melting point 150° (foam) $[\alpha]_D^{25} -31.2$ (c=1.06, acetone).

EXAMPLE 63

5-[1,4-dihydro-2,6-dimethyl-3-methoxycarbonyl-4-(2-chloro-3-trifluoromethyl-phenyl)-5-pyridylcarbonyl]isosorbide-2-acetate Melting point 220°–222° C. (from toluene) $[\alpha]_D^{25} +48.4$ (c=1.01, acetone).

Melting point 192°–194° C. (from toluene) $[\alpha]_D^{25} -68.0$ (c=0.99, acetone).

EXAMPLE 64

5-[1-4,dihydro-2,6-dimethyl-3-methoxycarbonyl-4-(2-chloro-3-trifluoromethyl-phenyl)-5-pyridylcarbonyl]isosorbide melting point 195°–196° C. (from toluene) $[\alpha]_D^{25} +45.9$ (c=1.26, acetone).

Melting point 177°–182° C. (from toluene $[\alpha]_D^{25} -63.5$ (c=1.06, acetone).

PREPARATION 1

Preparation of 2-chloro-3-trifluoromethylbenzaldehyde

2-Chloro-1-trifluoromethylbenzene (54.15 g) was dissolved in dry tetrahydrofuran (500 ml) and stirred while cooling to −68° under a stream of dry nitrogen. (The whole reaction is carried out under dry nitrogen until the addition of distilled water.) To this was added n-butyl lithium (180 ml of a 1.6M solution in hexane) dropwise keeping the temperature below −60°. After stirring at −68° for a further 2 hours, a solution of dimethylformamide (22 ml) in dry tetrahydrofuran (100 ml) was added dropwise keeping the temperature below −60°. The reaction mixture was allowed to warm to room temperature slowly over 17 hours and distilled water (200 ml) was then added. The organic phase was separated off and the aqueous liquors were extracted with ether (100 ml). The combined ether extracts plus the organic phase were washed with saturated brine, dried (MgSO₄), filtered and evaporated to give 61.5 g of a orange oil, being the crude title compound.

This oil was then added to an aqueous sodium bisulphite solution (65 g in 600 ml distilled water) and heated at 60° for 0.5 hours. The solution was extracted with methylene chloride (3×100 ml) and, after acidification of the aqueous phase with concentrated sulphuric acid to pH 1.0, was heated at 100° for a further 0.5 hours. The resultant aqueous solution was extracted with methylene chloride (3×200 ml) and the combined organic extracts were dried (MgSO₄), filtered and evaporated to give 42 g of a colourless solid which was crystallised from hexane to give the title compound, m.p. 43°–44°.

Analysis %: Found: C,45.9; H,2.0; Calculated for $C_8H_4F_3ClO$: C,46.1; H,2.0.

PREPARATION 2

Preparation of 2,3-dichlorobenzaldehyde

A similar route to that described in the previous Example, starting from 1,2-dichlorobenzene, proved to be a superior method for preparing the title compound, m.p. 62°.

Analysis %: Found: C,47.62; H,2.38; Calculated for $C_7H_4Cl_2O$: C,48.04; H,2.30.

We claim:

1. A compound of the general formula

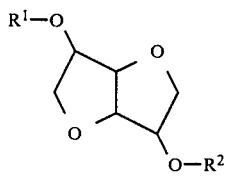

or a pharmaceutically acceptable salt thereof, wherein:

$R^1$ is hydrogen, lower acetyl having 2 to 5 carbon atoms, pyridylcarbonyl or nitro;

$R^2$ is a 1,4-dihydropyridylcarbonyl radical of the general formula

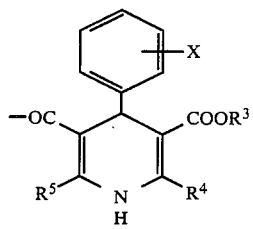

X is hydrogen, 1,2 or 3 of the same of different substituents selected from the group consisting of alkoxy, alkyl, cyano, dialkylamino, halogen, nitro and trifluoromethyl, or methylenedioxy;

$R^3$ is a saturated or unsaturated hydrocarbon radical having 1 to 5 carbon atoms optionally interrupted by an oxygen atom, or the hydrocarbon radical or the oxygen-interrupted hydrocarbon radical substituted by cyano; and $R^4$ and $R^5$ are the same or different and are in each case a lower alkyl group.

2. A compound according to claim 1 which is a derivative of 1,4:3,6-dianhydro-L-iditol (isoidide).

3. A compound according to claim 1 which is a derivative of 1,4:3,6-dianhydro-D-glucitol (isosorbide).

4. A compound according to claim 1 which is a derivative of 1,4:3,6-dianhydro-D-mannitol (isomannide).

5. A compound according to claim 1 which is 5-[1,4-dihydro-2,6-dimethyl-3-methoxycarbonyl-4-(3-nitrophenyl)-5-pyridylcarbonyl]isosorbide.

6. A compound according to claim 1 which is 5-[1,4-dihydro-2,6-dimethyl-3-methoxycarbonyl-4-(2-nitrophenyl)-5-pyridylcarbonyl]isosorbide.

7. A compound according to claim 1 which is 5-[1,4-dihydro-2,6-dimethyl-3-methoxycarbonyl-4-(2,3-dichlorophenyl)-5-pyridylcarbonyl]-isosorbide.

8. A compound according to claim 1 which is 5-[1-4,dihydro-2,6-dimethyl-3-methoxycarbonyl-4-(2-chloro-3-trifluoromethyl-phenyl)-5-pyridylcarbonyl]-isosorbide.

9. A pharmaceutical composition comprising an antihypertensive effective amount of a compound according to claim 1 and a pharmaceutically accceptable carrier or additive.

10. A method for controlling cardiovascular disease comprising the step of administering a vasodilatory effective amount of a compound according to claim 1.

11. A pharmaceutical composition comprising a vasodilatory effective amount of a compound according to claim 1 and a pharmaceutically acceptable carrier or additive.

* * * * *